(12) United States Patent
Cheung et al.

(10) Patent No.: US 8,868,349 B2
(45) Date of Patent: Oct. 21, 2014

(54) METHODS, SYSTEMS, AND PRODUCTS FOR QUANTITATIVELY MEASURING THE DEGREE OF CONCORDANCE BETWEEN OR AMONG MICROARRAY PROBE LEVEL DATA SETS

(75) Inventors: Philip Cheung, San Diego, CA (US); Timothy P. Tully, Solana Beach, CA (US); Humberto Ortiz-Zuazaga, San Juan, PR (US); Oscar Moreno, Rio Piedras, PR (US)

(73) Assignee: Dart Neuroscience (Cayman) Ltd., Camana Bay, Grand Cayman (KY)

( * ) Notice: Subject to any disclaimer, the term of this patent is extended or adjusted under 35 U.S.C. 154(b) by 640 days.

(21) Appl. No.: 12/772,030

(22) Filed: Apr. 30, 2010

(65) Prior Publication Data

US 2011/0093206 A1 Apr. 21, 2011

Related U.S. Application Data (60) Provisional application No. 61/174,313, filed on Apr. 30, 2009.

(51) Int. Cl.
*G01N 33/48* (2006.01)
*G06F 19/24* (2011.01)
*G06F 19/20* (2011.01)

(52) U.S. Cl.
CPC ............... *G06F 19/24* (2013.01); *G06F 19/20* (2013.01)
USPC .......................................................... 702/19

(58) Field of Classification Search
CPC ......... G06F 17/18; G06F 19/18; G06F 19/20; G06F 19/24; G06F 19/3443; G01N 2800/52; G06K 9/6231; G06K 9/6262
See application file for complete search history.

(56) References Cited

U.S. PATENT DOCUMENTS

| | | | |
|---|---|---|---|
| 6,516,276 B1 * | 2/2003 | Ghandour et al. | 702/27 |
| 2004/0019466 A1 | 1/2004 | Minor et al. | |
| 2004/0053317 A1 | 3/2004 | Glinski | |
| 2006/0173663 A1 | 8/2006 | Langheier et al. | |

FOREIGN PATENT DOCUMENTS

WO 2007023903 A1 3/2007

OTHER PUBLICATIONS

Carter, et al., BMC Bioinformatics vol. 6, No. 107, pp. 1-15 (2005).
Canales, et al., Nature Biotechnology vol. 24, No. 9, pp. 1115-1122 (2006).
Dudoit et al., "Statistical methods for identifying differentially expressed genes in replicated cDNA microarray experiments." Stanford University School of Medicine. Technical report # 578, Aug. 2000 (online), (retrieved on Jul. 14, 2010). <URL:gttp://citeseerx.ist.psu,edu/viewdoc/download?doi=10.1.1.37.943&rep=rep1&type=pdf>, pp. 2-38.

* cited by examiner

*Primary Examiner* — Eric S Dejong
(74) *Attorney, Agent, or Firm* — Don J. Pelto, Esquire; Sheppard, Mullin, Richter & Hampton LLP (57) ABSTRACT

Methods, systems and products are provided to quantitatively measure the degree of concordance between or among microarray probe level data sets. These can include the steps of evaluating outlier probe values, determine gene expression scores, evaluating the significant treatment effect for each gene expression score, and determining concordance between replicate data sets.

23 Claims, 7 Drawing Sheets

METHODS, SYSTEMS, AND PRODUCTS FOR QUANTITATIVELY MEASURING THE DEGREE OF CONCORDANCE BETWEEN OR AMONG MICROARRAY PROBE LEVEL DATA SETS

RELATED APPLICATION INFORMATION

This application claims the benefit of U.S. Provisional 61/174,313, filed Apr. 30, 2009. The entire teachings of this application are incorporated herein by reference.

FIELD OF THE INVENTION

The present invention relates to methods, systems and products for analyzing data obtained from arrays, more particularly microarrays.

BACKGROUND OF THE INVENTION

High density arrays such as microarrays are well-known and widely used to generate information about biological systems. Analysis of the data obtained from such arrays may be used in the development of new drugs and new diagnostic tools. However, the analysis of such data may be quite complex. In many such systems there are multiple sources of experimental error in the system. One way to reduce errors is to use replicate arrays in an experiment. However, even with replicate arrays it may be difficult to discern whether differences shown in the microarray data sets are genuine. Hence there is a need in the art for improved methods, systems, and products to reliably identify true positives in microarray-based experiments. The present invention meets these and other needs in the art,

SUMMARY OF THE INVENTION

In some embodiments, the present invention is a computer implemented method for analyzing the concordance between two or more microarray data sets (microarray data sets). In some embodiments the method includes measuring quantitatively the degree of concordance between or among two or more microarray data sets, where the measuring step comprises: summarizing the data obtained for each probe set present in a plurality of probe-level microarray data sets, wherein the summarizing comprises: discretizing each probe separately by comparing each probe value to the mean of the control values, resulting in a plurality of probe value calls wherein each of the plurality of probe value calls represents a distinct outcome or probability of an outcome; and performing majority logic decoding to summarize all repetitive probe value calls into a single call for each outcome; quantifying the degree of concordance between and/or among the summarized data from each probe-level microarray data set by utilizing a weighted variant of mutual information that assigns a particular weight reflecting the probability of an outcome; and using a scoring technique to measure the relative degree of concordance between or among the two or more data sets; and producing an output indicating the measured quantitative degree of concordance.

In further embodiments, the plurality of probe-level microarray data sets is two probe-level microarray data sets. In yet other embodiments, the weighted variant of mutual information is represented by the formula:

$$I(X, Y) = \sum_{y \in Y} \sum_{x \in X} w(x, y) p(x, y) \log\left(\frac{p(x, y)}{p(x)p(y)}\right)$$

wherein w(x,y) is the weight assigned to the combination of symbols x and y, described below, p(x,y) is the probability of the combination of symbol x and y, and p(x) is the frequency of symbol x in the sequence X. In some such embodiments, weights are assigned to w(x,y) are selected from the group consisting of 1.0 if x=y and x,y≠?, 0.5 if x=? or y=?, and 0.

In other embodiments the plurality of microarray probe-level data sets is three probe-level microarray data sets. In some such embodiments the weighted variant of mutual information is represented by the formula $$I(X, Y, N) = \sum_{y \in Y} \sum_{x \in X} \sum_{n \in N} w(x, y, n) p(x, y, n) \log\left(\frac{p(x, y, n)}{p(x)p(y)p(n)}\right)$$

wherein w(x,y,n) is the weight assigned to the combination of symbols x, y, and n for any number of data sets n described below, p(x,y,n) is the probability of the combinations of symbol x, y, and n for any number of data sets n, and p(x) is the frequency of symbol x in the sequence X. In some such embodiments, weights are assigned to w(x,y,n) as follows:

| Weight assigned to w(x, y, n) | Condition(s) |
|---|---|
| 1.0 | if x = y = n and x, y, n ≠ ? |
| 0.5 | if x = ? or y = ? or n = ? |
| 0 | otherwise |

In other embodiments, the probe-level microarray data sets are obtained from the same microarray platform. In further embodiments, the probe-level microarray data sets are obtained from a plurality of microarray platforms. In certain embodiments, the plurality of microarrays consists of a plurality of substantially identical microarray platforms. In yet other embodiments, the plurality of microarrays comprises at least two different microarray platforms. In some embodiments, the scoring technique comprises creating summed weighted mutual information (SWMI) by summing the weighted mutual information among all compared probe sets to obtain a SWMI score, which can then be compared on a relative basis to other SWMI and SWAMI (summed weighted averaged mutual information) scores. In some such embodiments the summing the weighted mutual information comprises a Huber regression, a Cauchy regression, or a fair regression.

In some embodiments, the microarray data sets are obtained from an DNA array, a cDNA array, a RNA array, a protein array, a tissue array or a chemical compound array. In some embodiments, the microarray data sets are obtained from a cDNA array. In some embodiments, the outcome and probe values each relates to gene expression; and wherein the probe value calls comprise a call for upregulation compared to the control, downregulation compared to the control, regulation within epsilon of the control, and an ambiguous probe value.

In other embodiments, the present invention may include systems capable of analyzing the concordance between two or more microarray data sets. In some embodiments, the system includes a processor; and a memory coupled with the processor, the memory storing a plurality of machine instructions that cause the processor to perform a plurality of logical steps when implemented by the processor. In some embodiments, the logical steps include those capable of executing one or more methods of the present invention.

In yet other embodiments, the present invention is a computer program product, including a computer usable medium having a computer readable program code embodied therein, the computer readable program code adapted to be executed to implement a method for analyzing the concordance between two or more microarray data sets. In some embodiments, the computer readable program code adapted to be executed to implement one or more of embodiments of the methods described herein.

In some embodiments, the present invention is directed to computer-implemented methods, systems, and computer program products directed to quantitatively measure the degree of concordance between or among microarray probe level data sets. These can include the steps of evaluating outlier probe values, determining gene expression scores, evaluating the significant treatment effect for each gene score, and determining concordance between replicate data sets. Evaluating outlier probe values can include (i) applying data transformation to satisfy the underlying assumptions for statistical analysis, (ii) applying computations to correct for global differences in fluorescence levels among microarray chips, (iii) removing microarray chips from the analysis that contain a percentage of outlier probe values for that chip greater than a defined threshold; (iv) reiterating steps (i)-(iii) whenever a chip is removed in step (iii) until there are no more chips with a percentage of outlier probe values above the defined threshold, and (v) masking on all chips all replicates of probes that include at least one outlier. In some embodiments, the assumptions for statistical analysis in step (i) are normality of error variance and homogeneity of error variance across the range of signal intensities. In other embodiments, the defined threshold in step (iv) is greater than 2, 4, 6, 8, or 10 percent outlier probes. In still other embodiments, the critical P value squared when evaluating treatment effects for concordance is determined to yield a genome-wide, false positive rate near zero. In these methods, systems, and programs, the plurality of microarrays can comprises at least two substantially identical microarrays, different microarray platforms. Such microarrays can include data sets obtained from an DNA array, a cDNA array, a RNA array, a protein array, a tissue array, or a chemical compound array.

DETAILED DESCRIPTION

In the following paragraphs, the present invention will be described in detail by way of example with reference to enumerated formulas and the attached drawings. Throughout this description, the embodiments and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

The present invention provides methods, systems and products for quantitatively measuring the degree of concordance between or among two or more microarray probe-level data sets (or simply "microarray data sets"). Such a microarray data set is defined as one sampling, which in preferred embodiments comprises a sampling of replicate chips. For example, a data set can represent an analysis of a treatment effect on gene expression in a control (N=10) versus experimental (or "treatment") group (N=10), wherein the analysis would include on ten replicate chips for the control group and ten replicate chips for the experimental group.

In some embodiments, the present invention includes obtaining the data from one or more experiments, summarizing the data, measuring the concordance between data, and producing an output. Systems and products include those embodying the methods described herein.

Arrays and Data Generation

The arrays for use with the systems and methods described herein, may be any suitable array, including those commercially available from, for example, Affymetrix, Inc., Illumina, Inc., or Roche NimbleGen, Inc. For example, the arrays may be a high or very high density array utilizing nucleic acids (including DNA, cDNA, RNA), proteins, antibodies, antigens, tissue or other biological or chemical material. The arrays may be any suitable size and shape, including sizes as small as a conventional computer or silicone-based ship. Generally, the arrays are comprised of features or probes attached to a substrate. The substrate may be any suitable material, including glass or other materials. Substantially identical microarrays correspond to the same microarray platform, for example, an Affymetrix chip and an Affymetrix chip, as well as different versions of an Affymetrix chip. Different microarray platforms would include, e.g., an Affymetrix chip versus a Roche NimbleGen chip.

The systems and methods described herein may be used with arrays employed for any suitable experiment, for determining any suitable outcome. An outcome may be any scientifically useful information, for example, any biological function, chemical function, biological or chemical function-structure relationship, gene expression levels, presence or absence of a protein, antibody, or nucleic acid in a target. A protein or antibody array may, for example, be used to determine the presence or amount of a substance in the target, to identify the substrates of protein kinases, to identify protein-protein interactions, or to identify the targets of small molecules. A tissue array may, for example, be used for histological studies, such as in situ hybridization. A chemical compound array may, for example, be used to determine which proteins bind to a chemical compound or to search potential drugs for therapeutic targets. A DNA array may, for example, be used to detect gene expression levels or to identify single nucleotide polymorphisms.

The experiments may be run in any suitable manner. For example, the features on the array may comprise nucleic acids, that are specifically arranged on the substrate such that their location is known. The arrays may then be exposed by any suitable method to a sample containing targets that may or may not associate with the features or probes. For example the targets may contain nucleic acid fragments complementary to a nucleic acid probe. The probes and targets are generally configured in a manner that provides a discernable signal when such association occurs. For example, the nucleic acid in the target may be labeled with radioactive or fluorescent molecules. The presence of this discernable signal and the knowledge of the identity and locations of the probes on the array permits analysis of the composition of the target. Such analysis may, for example, allow one to determine the level of expression of specific genes in the target.

Methods

Figure 1:
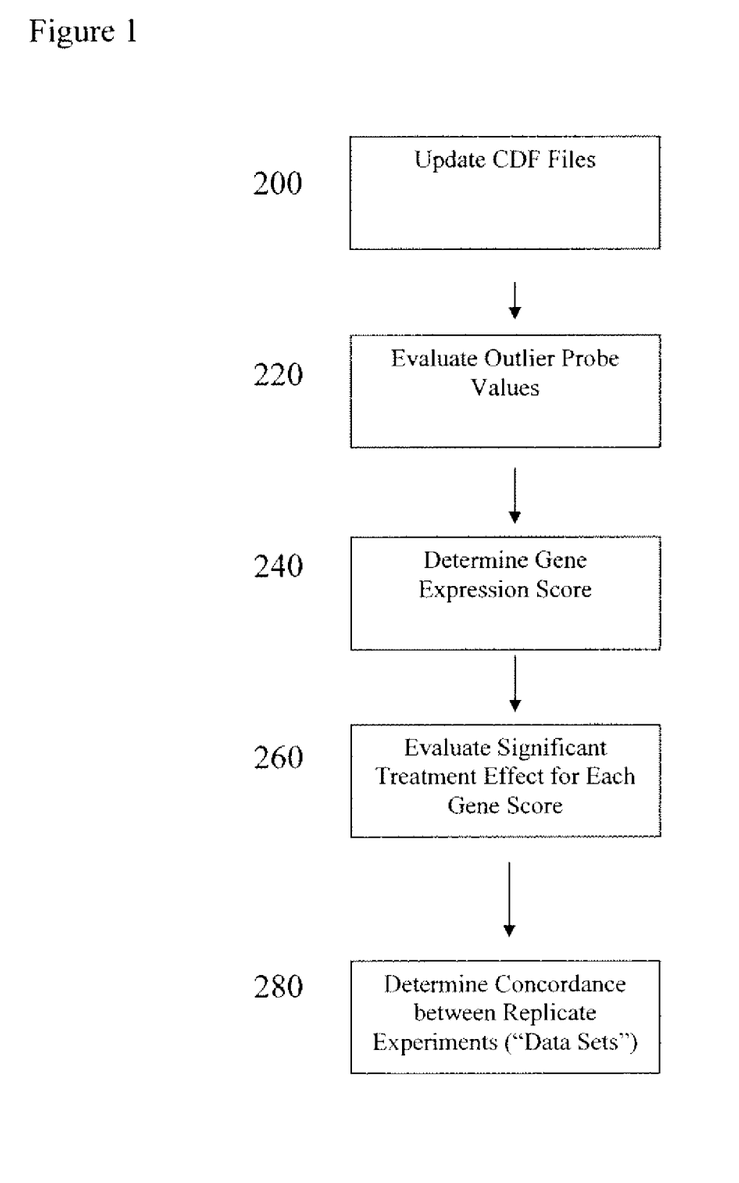
FIG. 1 is a flowchart depicting an embodiment of a method of the present invention.

FIG. 1 depicts a flow chart showing the conceptual steps of analysis. These include steps to Update CDF Files (200); Evaluate Outlier Probe Values (220); Determine Gene Expression Score (240); Evaluate Significant Treatment Effect for Each Gene Score (260); and Determine Concordance between Replicate Experiments ("Data Sets") (280). The embodiments are not necessarily limited to these steps and may include analyses that have additional steps, missing steps, or modifications to existing steps.

Majority Logic Decoding

As discussed herein, an initial step can include updating chip definition file (CDF) to ensure the most accurate updates regarding probe set definitions and gene identifiers.

In one embodiment, significant treatment effects for each gene are determined by an approach involving majority logic decoding. Previously, where arrays having DNA or cDNA probes are used in experiments to determine gene expression in the target, the summarization step has been performed under the assumption that each gene was represented by a single probe, as is typical of such cDNA arrays (H. Ortiz-Zuazaga, S. Peña de Ortiz, and O. Moreno de Ayala, "Error correction and clustering gene expression data using majority logic decoding," in *Proceedings of The* 2007 *International Conference on Bioinformatics and Computational Biology* (*BIOCOMP* '07), Las Vegas, Nev., USA, Jun. 25-28, 2007). That summarization method corrected the probe-level data for errors by first discretizing each probe separately through comparing each expression value to the mean of the control values and then performing majority logic decoding to summarize all probe values from multiple repetitions into a single call for each gene.

In certain embodiments, the present invention extends this method to multiple probes. In such embodiments the prior method is applied to the data, treating each probe as a separate entity. This summarizes the repetitions, resulting in a set of calls for each probe. A call is a symbol or value assigned to a particular outcome. For example, a call may be an indicator that a certain percentage of probes provided a discernable signal after exposure to the target. In an example where gene expression is evaluated a call is "+" if a probe is upregulated compared to the control, "−" if the probe is downregulated compared to the control, "0" if the probe is within the epsilon of the control, and "?" if the results are ambiguous. Indeed, any appropriate symbols may be used. In such an embodiment, majority logic decoding is then performed on the set of probes corresponding to each gene as described in the previous literature.

Table 1 illustrates the majority logic decoding results for an example probe set. In the example set, each of 4 genes is represented by 14 probes, though obviously any suitable number genes and genes per probe may be used. For example, from 1 to 1000 genes may be analyzed and each may have from 1 to 10,000 probes per gene. If a set of probes has more than a certain number of symbols in agreement that consensus symbol (e.g., a "+" if more the probe is upregulated compared to the control) is used, otherwise the symbol "?" is used to denote an ambiguous call. Indeed, any appropriate symbols may be used. In some embodiments, a consensus requires 50% or more of the probes having a given result. For example, if there are 14 probes, as in this example, 7 probes would have to be in agreement for a consensus symbol to be used. In other embodiments, from about 50% to about 95% consensus may be required. In further embodiments, about 55%, 60%, 65%, 70%, 75%, 80%, 85%, 90%, 95% or about 99% may be required for a consensus. In the present example, there are 14 rows (each depicting one of the 14 probes per gene) and 4 columns (each representing a gene), and in the result each column is set to the symbol occurring more than 7 times in the data. At the bottom of the table, the majority logic decoding result or "mld" is shown, which represents the consensus symbol, or the ambiguous symbol, as applicable, for each column.

TABLE 1

Majority logic decoding results ('mld') for an example probe set.

[['0', '−', '0', '+'],
['0', '−', '+', '+'],
['0', '−', '0', '+'],
['0', '−', '+', '+'],
['0', '−', '+', '+'],
['−', '−', '0', '0'],
['0', '−', '0', '+'],
['0', '−', '0', '+'],
['−', '−', '−', '0'],
['0', '−', '0', '+'],
['−', '−', '0', '0'],
['0', '−', '0', '+'],
['0', '−', '0', '+'],
['0', '−', '+', '+']]
'mld' = ['0', '−', '0', '+']

Analyze concordance step 260, involves the comparison of multiple microarray data sets to one another in an attempt to reach one or more conclusion as to the results or outcomes. For example, if an experiment has been carried out on different microarray technologies, concordance is used to determine which genes demonstrate the same patterns of gene expression in the two data sets.

In one embodiment, concordance can be applied to the comparison of two independent data sets, each representing a repetition of the same experiment. In turn, each experiment might involve comparing two groups with respect to a specified variable, such as a comparison of gene expression in cells treated with and without a drug. As disclosed herein, this concept of concordance represents a statistically powerful approach on a genome-wide level to greatly reduce the identification of false positive in microarray analyses.

In some embodiments, the calculation is performed as part of a larger process. In other embodiments, a particular program performs the calculation.

Mutual Information

In some embodiments, such as those based on data sets summarized by majority logic coding, the degree of concordance between the data sets is determined using mutual information. Mutual information can measure both positive correlation (e.g., similar patterns of expression in an independently replicated experiment) and negative correlation (e.g., opposite patterns of expression in an independently replicated experiment).

In preferred embodiments, weighted mutual information is used to select genes that only shown very similar patterns of expression—and not opposite patterns. In some embodiments, the present invention uses the weighted variant of mutual information in Equation 1 where w(x,y) is the weight assigned to the combination of symbols x and y, described below, p(x,y) is the probability of the combination of symbol x and y, and p(x) is the frequency of symbol x in the sequence X.

Equation 1. Weighted Variant of Mutual Information Used when Quantitatively Measuring the Concordance Between Two Microarray Data Sets.

$$I(X, Y) = \sum_{y \in Y} \sum_{x \in X} w(x, y) p(x, y) \log\left(\frac{p(x, y)}{p(x)p(y)}\right)$$

In some embodiments, for example, an embodiment where one is trying to determine whether or not a certain gene or genes is expressed in a target, the weights are set such that similar patterns of expression are given higher weights, and opposite patterns of expression are given lower weight. Ambiguous calls are given an intermediate weight. Weights assigned to w(x,y) when quantitatively measuring the degree of concordance between two microarray data sets are shown in Table 2.

TABLE 2

Weights assigned to w(x, y) in embodiments of the present invention which quantitatively measure the degree of concordance between two microarray data sets.

| Weight assigned to w(x, y) | Condition(s) |
| --- | --- |
| 1.0 | if x = y and x, y ≠ ? |
| 0.5 | if x = ? or y = ? |
| 0 | all other values of x and y |

An example of such an embodiment of the present invention is illustrated in Table 3 and Equation 2, below. Table 3 depicts two sets of calls for an example probe set found in both of two microarray data sets, and Equation 2 shows the computation of the WMI for these two probe sets.

TABLE 3

Example calls for a single probe set found within both of two microarray data sets.

ac = ['0', '−', '0', '+']
nc = ['0', '−', '−', '−']

Equation 2. Computation of WMI for Example Calls from Table 3.

$$I(ac, nc) = w(0, 0)p(0, 0)\log\left(\frac{p(0, 0)}{p(0)p(0)}\right) + w(-, -)p(-, -)\log\left(\frac{p(-, -)}{p(-)p(-)}\right) +$$

$$w(0, -)p(0, -)\log\left(\frac{p(0, -)}{p(0)p(-)}\right) + w(+, -)p(+, -)\log\left(\frac{p(+, -)}{p(+)p(-)}\right) =$$

$$1 \cdot 1/4 \cdot \log\left(\frac{1/4}{2/4 \cdot 1/4}\right) + 1 \cdot 1/4 \cdot \log\left(\frac{1/4}{1/4 \cdot 1/4}\right) +$$

$$0.1 \cdot 1/4 \cdot \log\left(\frac{1/4}{2/4 \cdot 3/4}\right) + 0.1 \cdot 1/4 \cdot \log\left(\frac{1/4}{1/4 \cdot 3/4}\right) = 0.35$$

In certain other embodiments, the concordance among more than two microarray data sets is measured. In those embodiments, a variant of the equation shown in Equation 1 is used. This equation is shown in Equation 3 where w(x,y,n) is the weight assigned to the combination of symbols x, y, and n for any number of microarray data sets n described below, p(x,y,n) is the probability of the combinations of symbol x, y, and n for any number of microarray data sets n, and p(x) is the frequency of symbol x in the sequence X. In such embodiments, the weights assigned to w(x,y,n) are listed below in Table 4.

Equation 3. Weighted Variant of Mutual Information Used when Quantitatively Measuring the Concordance Among More than Two Microarray Data Sets.

$$I(X, Y, N) = \sum_{y \in Y} \sum_{x \in X} \sum_{n \in N} w(x, y, n) p(x, y, n) \log\left(\frac{p(x, y, n)}{p(x)p(y)p(n)}\right)$$

TABLE 4

Weights assigned to w(x, y, n) in embodiments of the present invention which quantitatively measure the degree of concordance among more than two microarray data sets.

| Weight assigned to w(x, y, n) | Condition(s) |
| --- | --- |
| 1.0 | if x = y = n and x, y, n ≠ ? |
| 0.5 | if x = ? or y = ? or n = ? |
| 0 | otherwise |

An example of such an embodiment of the present invention is illustrated in Table 5 and Equation 4, below. Table 5 depicts three sets of calls for an example probe set found in each of three microarray data sets, and Equation 4 shows the computation of the WMI for these three probe sets.

TABLE 5

Example calls for a single probe set found within each of three data sets.

ac = ['0', '−', '0', '+']
nc = ['0', '−', '−', '−']
rc = ['0', '?', '−', '+']

Equation 4. Computation of WMI for Example Calls from Table 5.

$$I(ac, nc, rc) =$$

$$w(0, 0, 0)p(0, 0, 0)\log\left(\frac{p(0, 0, 0)}{p(0)p(0)p(0)}\right) + w(-, -, ?)p(-, -, ?)$$

$$\log\left(\frac{p(-, -, ?)}{p(-)p(-)p(?)}\right) + w(0, -, -)p(0, -, -)\log\left(\frac{p(0, -, -)}{p(0)p(-)p(-)}\right) +$$

$$w(+, -, +)p(+, -, +)\log\left(\frac{p(+, -, +)}{p(+)p(-)p(+)}\right) =$$

$$1 \cdot 1/4 \cdot \log\left(\frac{1/4}{2/4 \cdot 1/4 \cdot 1/4}\right) + 0.5 \cdot 1/4 \cdot \log\left(\frac{1/4}{1/4 \cdot 1/4 \cdot 1/4}\right) + 0.1 \cdot$$

$$1/4 \cdot \log\left(\frac{1/4}{2/4 \cdot 3/4 \cdot 1/4}\right) + 0.1 \cdot 1/4 \cdot \log\left(\frac{1/4}{1/4 \cdot 3/4 \cdot 1/4}\right) = 0.42$$

The present invention further provides a novel scoring method for measuring the degree of agreement between or among two or more microarray data sets.

In certain embodiments, the probe sets contained in both or each of the microarrays map only to one probe set on each microarray it is compared to, and in those embodiments a SWMI (summed weighted mutual information) scoring technique is used to measure the relative degree of concordance between or among the microarray data sets. To obtain the SWMI score, the weighted mutual information among all compared probe sets is summed together in order to obtain one overall SWMI score, which can then be compared on a relative basis to other SWMI and SWAMI scores.

In certain other embodiments, the probe sets contained in both or each of the microarrays map to more than one probe set on any microarray it is compared to, and in those embodiments a SWAMI (summed weighted averaged mutual information) scoring technique is used to measure the relative degree of concordance between or among the microarray data sets. To obtain the SWAMI score, the weighted mutual information resulting from any one probe set that maps to more than one probe set on any microarray it is compared to is averaged, and the averaged weighted mutual information among all compared probe sets is summed together in order to obtain one overall SWAMI score, which can then be compared on a relative basis to other SWMI and SWAMI scores.

The average may be done by any suitable method. In some embodiments, the averaging is done by one or more regression analyses. In some embodiments the regression may be linear or robust. In some embodiments, the regression is a Huber regression, a Cauchy regression, or a fair regression.

The SWMI or SWAMI score measures mutual information between and among microarray data sets, but is weighted by a score to produce biologically meaningful correlation: sequences cannot be inversely correlated and still have a high SWMI or SWAMI score. The SWMI or SWAMI score leads to a list of probe sets that in some sense optimize two biologically relevant criteria. First, the probe sets should be informative in the sense that they take on a range of values; and second, the probe sets should be consistent between the two microarray data sets.

In another embodiment, significant treatment effects for each gene are determined by an approach called Normask, as depicted schematically in FIG. 8.

Update CDF Files:

In preferred embodiments, chip definition files (CDFs) are reevaluated to ensure that probe set definitions reflect the latest updates. That is, probes on microarrays have traditionally been grouped into probe sets, each of which is designed to represent a single gene. As the genomic knowledge of organisms has evolved, the probes and probe sets have also changed, which can result incorrect mapping. The files from a chip can therefore be read in computationally and used to confirm and update the relationships between the probes, probe sets, and genes from the CDFs. This step therefore helps to reduce discrepancies in gene definitions before the processing the data on the chip.

Evaluate Outlier Probe Values:

In selected aspects, the method includes one or more steps to evaluate error in the primary microarray data. Such steps may include the following:

Data Transformation

Various methods of data transformation are applied to satisfy underlying assumptions for statistical analysis, in particular the assumptions of normality of error variance and homogeneity of error variance across the range of signal intensities Chip Normalization Preferred embodiments include computations that correct for global differences in fluorescence levels among chips, which may arise, for example, from different amounts of sample used in the experiment.

Identification of Outlier Probe Values

An outlier probe value is defined as that which is more than three standard deviations from the mean of all replicate values for that probe.

Quality Control: Chip Removal

Certain embodiments include steps to remove microarray chips that contain a percentage of outlier probe values for that chip greater than a defined threshold. For example, chips having greater than 2, 4, 6, 8, or 10 percent outlier probes may be selected for removal from the analysis. Available methods for such removal can include NUSE, RLE, RNA Deg Plot, SimplyAffy, etc. Whenever a chip has been removed from the data set, the error evaluation process defined is reiterated. Preferably, this reiterative process continues until there are no more chips with the percentage of outlier probe values above the defined threshold.

Quality Control: Probe Masking

For chips remaining in the analysis, probes which include at least one outlier are masked from all chips. For example, if an outlier represents only one of the replicate probe values, all replicate values of that probe are removed from further analysis.

Determine Gene Expression Score:

A gene expression score is determined by combining the remaining probes for each probe set. Different procedures are available to generate such summarized values, such as median.polish, tukey.biweight, average.log, log.average, median.log, etc.

Evaluate Significant Treatment Effect for Each Gene Score:

In preferred embodiments, the evaluation of treatment effects is made by performing a statistical analysis of gene expression scores between two or more groups. To compare the two or more groups of gene expression scores, various statistical measures can be used, such as SAMS, LIMMA, the T-Test, or Bootstrap, etc. Such statistical analysis will result in a "gene call" for the experimental group that is either greater than control, less than control, or not different than control.

Determine Concordance Between Replicate Experiments ("Data Sets"):

Concordance is defined as the number of statistically significant gene calls, which occur in the same direction in both (all) data sets, divided by the total number of gene calls from either (all) data set(s).

Any of the statistical methods above will result in a particular false positive rate. The likelihood that a false positive would be present in the overlapping set of data for two independent microarray experiments is reduced to the false positive rate for a single experiment squared. In preferred embodiment, concordance is used to drive the false positive rate to near zero, thereby improving the identification of true positive treatment effects.

Conceptually, if concordance is determined using two identical microarray platforms, false positives from sampling error will be minimized but false positives from systematic artifacts inherent to the platform. To minimize this source of false positive, one embodiment defines concordance using two different microarray platforms.

If desired, the results from a Concordance analyses can be compared with other methods for analyzing different gene expression.

Systems

Figure 2:
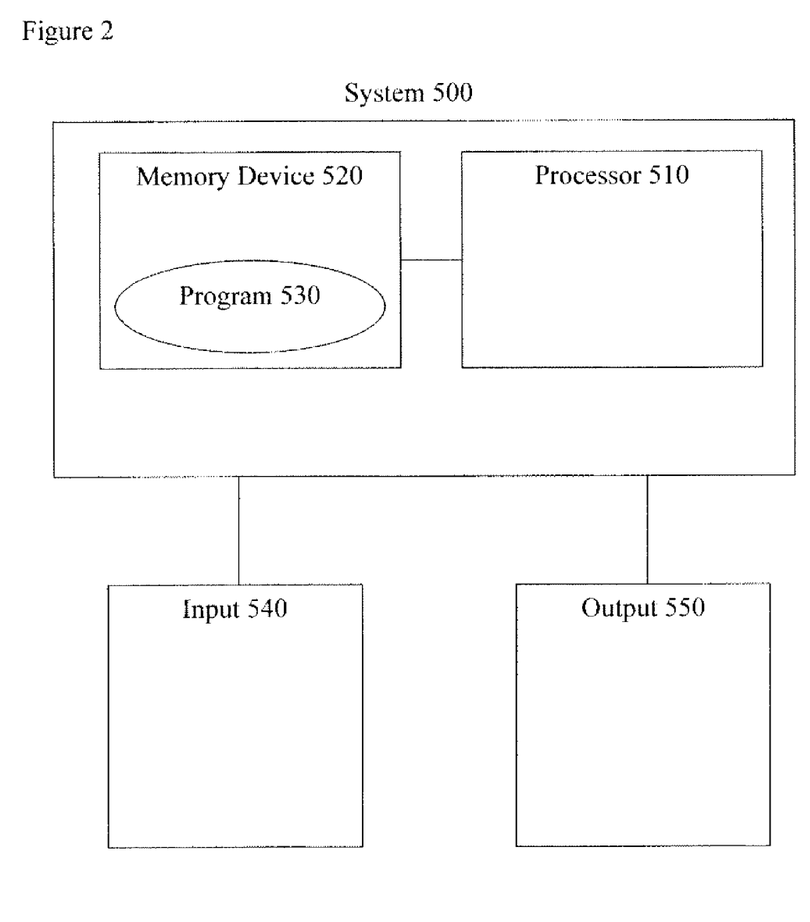
FIG. 2 depicts an embodiment of a system of the present invention.

In some embodiments, the present invention relates to systems for performing one or more of the methods described herein. An exemplary system 500 is depicted in FIG. 2. System 500 may, for example, perform an embodiment of data correction process 200. In other embodiments, system 500 may perform one or more steps of correction process 200, such as summarization step 140 or analyze concordance step 260, or any sub-steps thereof.

FIG. 2 is a basic schematic block diagram showing an embodiment of a system 500 of the present invention. System 500 has elements central processing unit (CPU) 510, memory device 520, and program 530. System 500 may be embodied in a single unit or multiple units functionally connected by any suitable means. Examples of single unit system 500 include a server, a microcomputer or the like. CPU 510 can be anything operable to retrieve, interpret, and/or execute program 530. In some embodiments, CPU 510 may be one or more microprocessors. For example, processor 510 could be any one of Intel Corporation's processors (e.g. Xeon®, Centrino®, Celeron®, or Pentium®), Advanced Micro Design, Inc.'s processors (e.g. Athlon™ or Sempron™), Sun Microsystem Inc.'s processors, or Motorola Inc.'s processors. Memory device 520 can be any computer readable medium. For example, memory device 520 could be a floppy disk, flash drive, external hard drive, hard drive, ROM chip, cd ROM, or the like. Program 530 includes computer readable instructions to carry out any embodiment of a process or method of the present invention, including those discussed with reference to FIG. 1 and all variations of those processes or methods. The computer readable instructions can be in any programming language.

Program Products

Figure 3:
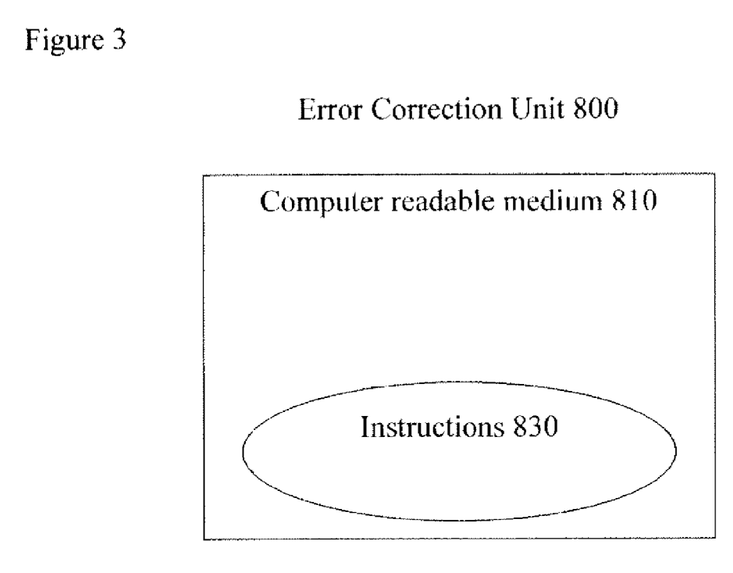
FIG. 3 is a schematic block diagram showing an embodiment of an article of manufacture of the present invention.

In some embodiments, the present invention may further relate to a computer program product for performing one or more methods of the present invention. An exemplary product, error correction unit 800 is depicted in FIG. 3. Unit 800 may, for example, contain instructions for performing an embodiment of data correction process 200. In other embodiments, unit 800 may include instructions for performing one or more steps of correction process 200, such as summarization step 140 or analyze concordance step 260, or any sub-steps thereof.

FIG. 3 shows an embodiment of an article of manufacture of the present invention. Computer readable medium 810 can be any such medium known in the art or not. For example, computer readable medium 810 could be a floppy disk, flash drive, external hard drive, hard drive, ROM chip, cd ROM, or the like. Instructions 830 are stored on computer readable medium 810. Instructions 830 enable a computer or like-machine or system, to perform an embodiment of a method or process of the present invention, including those discussed with reference to FIG. 1 and all variations of those processes or methods. Instructions 830 can be in any form, language, or format. Preferably, instructions 830 are in a form directly readable and executable by a computer or computer system.

All publications cited in this application are incorporated by reference in their entirety for all purposes to the same extent as if each individual publication were so individually noted.

Example 1

Quantitatively Measuring the Concordance Between One Affymetrix and One NimbleGen Array The methodology of the present invention was applied to a large data set obtained from an odor-avoidance training experiment with *Drosophila melanogaster*. The discretization and error correction procedure of the present invention was applied to two *Drosophila* microarray data sets, one Affymetrix (Affymetrix, Inc., Santa Clara, Calif., USA), one NimbleGen (Roche NimbleGen, Inc., Madison, Wis., USA), having multiple probes per gene. A file with the sequence annotations for every probe on the drosgenome1 chips, DrosGenome1.na21.accot.csv, was obtained from Affymetrix. The "Probe Set ID" and "Ensembl" columns were used to construct a map from the ID used by Affymetrix to the IDs used in the NimbleGen arrays. Several Affymetrix Probe Set IDs have more than one Ensembl ID listed. Because of this, the WMI for all NimbleGen probe sets that map to the same Affymetrix probe set was averaged.

The averaged WMI over all probe sets was summed to obtain the SWAMI score. In addition, the probe set list was sorted by the weighted averaged mutual information to produce a list of probe sets ranked according to how informative and how similar they are between the microarray data sets.

Normalization and Summarization Tests

A series of analyses was performed to test the effect of different transformations and summarization algorithms on the concordance between the two microarray data sets, as measured by the SWAMI score. The affyPLM package from BioConductor was used (R. C. Gentleman, V. J. Carey, D. M. Bates, B. Bolstad, M. Dettling, S. Dudoit, B. Ellis, L. Gautier, Y. Ge, J. Gentry, K. Hornik, T. Hothorn, W. Huber, S. Iacus, R. Irizarry, F. Leisch, C. Li, M. Maechler, A. J. Rossini, G. Sawitzki, C. Smith, G. Smyth, L. Tierney, J. Y. H. Yang, and J. Zhang, "Bioconductor: Open software development for computational biology and bioinformatics," *Genome Biology*, vol. 5, p. R80, 2004. [Online]. Available: http://genomebiology.com/2004/5/10/R80). A comparison of "log 2", "sqrt" and "cuberoot" transformations was set up on the expression values, and "Huber", "fair" and "Cauchy" methods of robust regression of the probe values. Once the summarized data was produced, the limma package from BioConductor was used to produce a discretization using the decideTests function (G. K. Smyth, "Linear models and empirical Bayes methods for assessing differential expression in microarray experiments." *Stat. Appl. Genet. Mol. Biol.*, vol. 3, p. Article3, 2004 and "Limma: linear models for microarray data." in *Bioinformatics and Computational Biology Solutions using R and Bioconductor*, R. Gentleman, V. Carey, S. Dudoit, R. Irizarry, and W. Huber, Eds. New York: Springer, 2005, pp. 397-420). These discretizations were compared between the two microarray data sets using the SWAMI score. Error correction and clustering procedures were run on the data summarized using the rma command from BioConductor (R. A. Izirrary, B. M. Bolstad, F. Collin, L. M. Cope, B. Hobbs, and T. P. Speed, "Summaries of Affymetrix genechip probe level data." *Nucleic Acids Res., vol.* 31, no. 4, p. e15, 2003).

Results

Table 6 summarizes the total SWAMI scores obtained for several different transformation and regression methods on the *Drosophila* data. The defaults for affyPLM are log 2 transformation and Huber regression, but sqrt transformation and fair regression yielded much better SWAMI scores on the data.

TABLE 6

SWAMI scores for several transformation and regression methods.

| Transformation | Regression | SWAMI |
|---|---|---|
| log2 | Huber | 182 |
| log2 | fair | 186 |
| log2 | Cauchy | 169 |
| sqrt | Huber | 212 |
| sqrt | fair | 230 |
| sqrt | Cauchy | 200 |
| cuberoot | Huber | 207 |
| cuberoot | fair | 216 |
| cuberoot | Cauchy | 202 |

Table 7 presents the SWAMI scores for various error correction techniques on the *Drosophila* data. All these scores are more than an order of magnitude higher than the scores for the affyPLM based methods. The highest score is the "trimmed mean" method, which discards repetitions which deviate most from the mean. In this case, two repetitions were discarded and eight repetitions were kept for each probe.

TABLE 7

SWAMI scores for error correction methods.

| Method | SWAMI |
|---|---|
| Trimmed mean | 3657 |
| Mean | 2535 |
| Consensus | 3058 |
| Consensus vs. mean control | 1525 |

Figure 4:
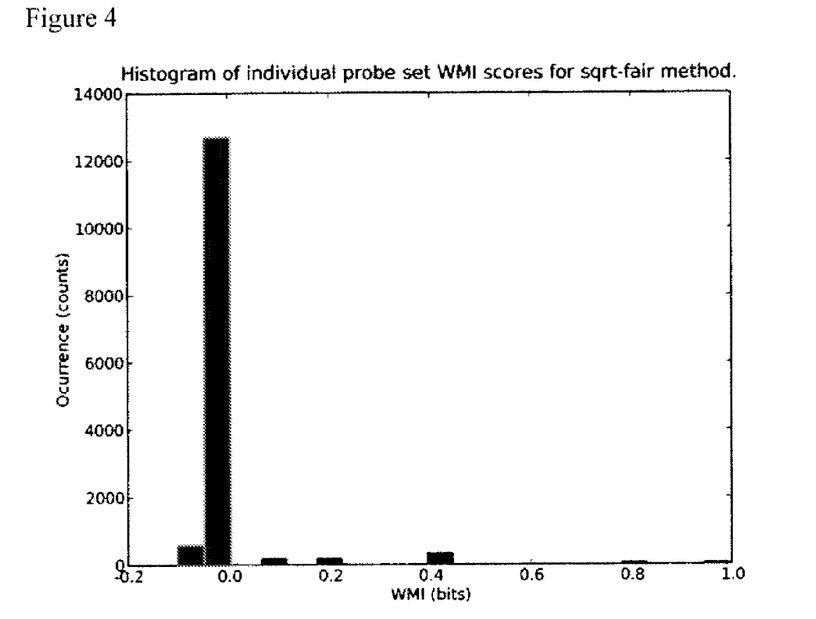
FIG. 4 depicts the distribution of weighted mutual information scores for individual probe sets in the sqrt-fair method.
Figure 5:
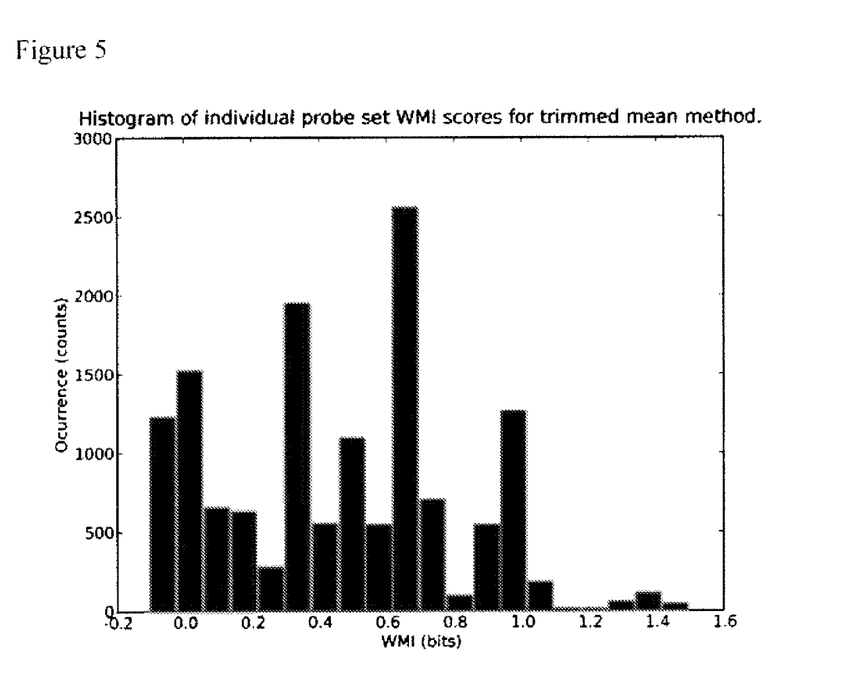
FIG. 5 depicts the distribution of WMI scores for individual probe sets in the trimmed mean method.

FIG. 4 and FIG. 5 show the frequency of the individual WMI scores per probe set for two representative methods, the sqrt-fair method, which obtained the best SWAMI score in Table 6, and the trimmed mean, the best performer in Table 7. The error correction methods show a wider distribution, whereas the affyPLM methods are very narrowly distributed around 0.

Figure 6:
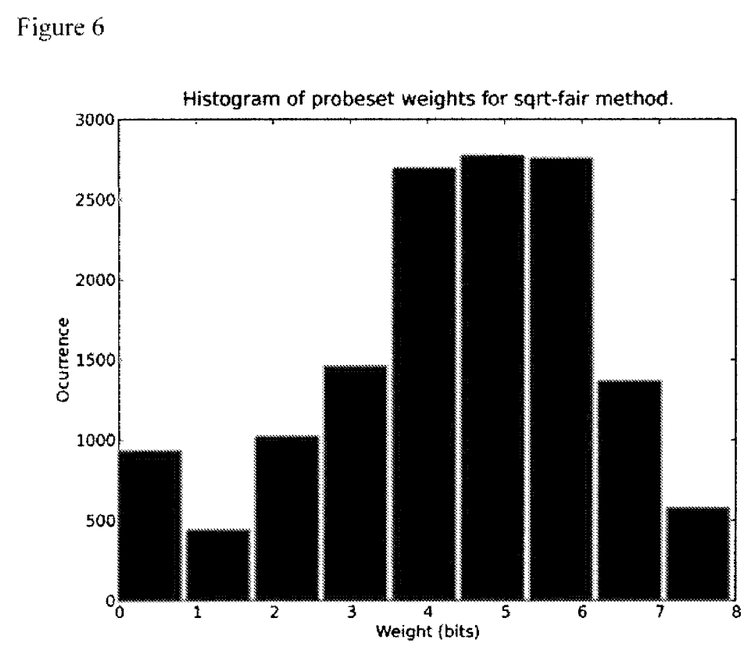
FIG. 6 depicts the distribution of nonzero calls for individual probe sets in the sqrt-fair method.
Figure 7:
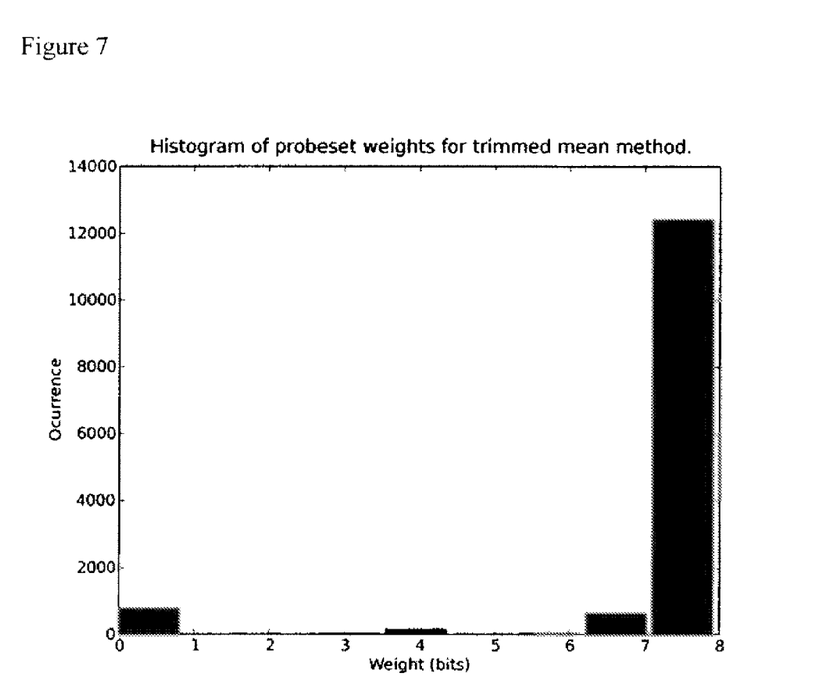
FIG. 7 depicts the distribution of nonzero calls for individual probe sets in the trimmed mean method.

FIG. 6 and FIG. 7 illustrate the distribution of nonzero calls in each probe set in the data. In binary vectors this would be called the "weight" of the vector. The sqrt-fair method produces calls distributed normally with mean around 5, whereas the trimmed mean method produces calls with nearly all entries nonzero.

The results indicate that the error correction procedure results in much higher SWAMI scores between two different microarray data sets than other more common analysis techniques. The first reason is that the set of calls produced by the other techniques have more "0" calls, indicating no significant change in expression, as seen in FIG. 6 where the weight peaks around 5. The majority logic decoding of the present invention results in calls with more "+" and "−" values, and therefore the weight illustrated in FIG. 7 is much higher. If these calls were not in agreement between microarray data sets, however, the SWAMI scores would not be high. Therefore, the error correction procedure of the present invention increases the degree of concordance between the microarray data sets, as measured by the SWAMI score.

Thus, it is seen that methods, systems, and computer program products for quantitatively measuring the degree of concordance between or among microarray data sets are provided. One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in this description may practice the invention as well While various embodiments of the present invention have been described above, it should be understood that they have been presented by way of example only, and not of limitation. Likewise, the various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present invention. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The invention claimed is:

1. A computer implemented method comprising:
analyzing quantitatively concordance between two or more microarray data sets, wherein the two or more microarray data sets comprise data from independent microarray experiments based on a plurality of replicate microarray chips, and wherein said analyzing step comprises:
   (1) updating chip definition files in each of the two or more microarray data sets, wherein the updating comprises scanning the chip definition files into a computer memory; and using a computer processor to compare information from the chip definition files with updated information for chip definition files, and to update a relationship between probes, probe sets, and gene definitions in each of the two or more microarray data sets;
   (2) evaluating outlier probe values in each of the two or more microarray data sets using a computer processor, wherein the evaluating comprises:
      (i) applying data transformation on each of the two or more microarray data sets to satisfy underlying assumptions for statistical analysis, wherein the assumptions for statistical analysis are normality of error variance and homogeneity of error variance across the range of signal intensities;
      (ii) applying data normalization to correct for global differences in fluorescence levels among microarray chips,
      (iii) removing data from replicate microarray chips from the analysis that contain a percentage of outlier probe values for that microarray chip greater than a defined threshold,
      (iv) reiterating steps (i)-(iii) whenever the data from a replicate microarray chip is removed in step (iii) until there are no more chips with a percentage of outlier probe values above the defined threshold, and
      (v) masking the data on all remaining microarray chips by removing from further analysis the values of all replicates of probes that include at least one outlier;
   (3) determining a gene expression score for the remaining probes of each probe set in each of the two or more microarray data sets;
   (4) evaluating treatment effects by performing a statistical analysis of gene expression scores between two or more groups in each of the two or more microarray data sets; and
   (5) determining concordance between the two or more microarray data sets.

2. The computer-implemented method of claim 1, wherein each of the two or more microarray data sets is obtained from the same microarray platform.

3. The method of claim 1, wherein in step (iv), the defined threshold is greater than 2, 4, 6, 8, or 10 percent outlier probes.

4. The method of claim 1, wherein a critical P value squared when evaluating treatment effects for concordance is determined to yield a genome-wide, false positive rate near zero.

5. The method of claim 1, wherein each of the two or more microarray data sets is obtained from substantially identical microarray platforms.

6. The method of claim 1 wherein each of the two or more microarray data sets is obtained from at least two different microarray platforms.

7. The method of claim 1, wherein each of the two or more microarray data sets is obtained from an DNA array, a cDNA array, a RNA array, a protein array, a tissue array, or a chemical compound array.

8. A system comprising:
a processor; and a memory coupled with the processor, the memory storing a plurality of machine instructions that cause the processor to perform a plurality of logical steps when implemented by the processor for analyzing quantitatively concordance between two or more microarray data sets, wherein the two or more microarray data sets comprise data from independent microarray experiments based on a plurality of replicate microarray chips, the logical steps comprising
   (1) updating chip definition files in each of the two or more microarray data sets, wherein the updating comprises scanning the chip definition files into the memory; and using the processor to compare information from the chip definition files with updated information for chip definition files, and to update a relationship between probes, probe sets, and gene definitions in each of the two or more microarray data sets;
   (2) evaluating outlier probe values in each of the two or more microarray data sets, wherein the evaluating comprises:
      (i) applying data transformation on each of the two or more microarray data sets to satisfy underlying assumptions for statistical analysis, wherein the assumptions for statistical analysis are normality of error variance and homogeneity of error variance across the range of signal intensities;
      (ii) applying data normalization to correct for global differences in fluorescence levels among microarray chips,
      (iii) removing data from replicate microarray chips from the analysis that contain a percentage of outlier probe values for that microarray chip greater than a defined threshold,
      (iv) reiterating steps (i)-(iii) whenever the data from a replicate microarray chip is removed in step (iii) until there are no more chips with a percentage of outlier probe values above the defined threshold, and
      (v) masking the data on all remaining microarray chips by removing from further analysis the values of all replicates of probes that include at least one outlier;
   (3) determining a gene expression score for the remaining probes of each probe set in each of the two or more microarray data sets;
   (4) evaluating treatment effects by performing a statistical analysis of gene expression scores between two or more groups in each of the two or more microarray data sets; and
   (5) determining concordance between the two or more microarray data sets.

9. The system of claim 8, wherein each of the two or more microarray data sets is obtained from the same microarray platform.

10. The system of claim 8, wherein in step (iv), the defined threshold is greater than 2, 4, 6, 8, or 10 percent outlier probes.

11. The system of claim 8, wherein a critical P value squared when evaluating treatment effects for concordance is determined to yield a genome-wide, false positive rate near zero.

12. The system of claim 8, wherein each of the two or more microarray data sets comprises substantially identical microarray platforms.

13. The system of claim 8, wherein each of the two or more microarray data sets comprises at least two different microarray platforms.

14. The system of claim 8, wherein each of the two or more microarray data sets is obtained from an DNA array, a cDNA array, a RNA array, a protein array, a tissue array, or a chemical compound array.

15. A computer program product, comprising a non-transitory computer usable medium having a computer readable program code embodied therein, said computer readable program code adapted to be executed to implement a method, said method comprising analyzing quantitatively concordance between two or more microarray data sets, wherein the two or more microarray data sets comprise data from independent microarray experiments based on a plurality of replicate microarray chips, and wherein the analyzing step comprises:
  (1) updating chip definition files in each of the two or more microarray data sets, wherein the updating comprises scanning the chip definition files into a computer memory; and using a computer processor to compare information from the chip definition files with updated information for chip definition files, and to update a relationship between probes, probe sets, and gene definitions in each of the two or more microarray data sets;
  (2) evaluating outlier probe values in each of the two or more microarray data sets using a computer processor, wherein the evaluating comprises:
    (i) applying data transformation on each of the two or more microarray data sets to satisfy underlying assumptions for statistical analysis, wherein the assumptions for statistical analysis are normality of error variance and homogeneity of error variance across the range of signal intensities;
    (ii) applying data normalization to correct for global differences in fluorescence levels among microarray chips,
    (iii) removing the data from replicate microarray chips from the analysis that contain a percentage of outlier probe values for that microarray chip greater than a defined threshold,
    (iv) reiterating steps (i)-(iii) whenever the data from a replicate microarray chip is removed in step (iii) until there are no more chips with a percentage of outlier probe values above the defined threshold, and
    (v) masking the data on all remaining microarray chips by removing from further analysis the values of all replicates of probes that include at least one outlier;
  (3) determining a gene expression score for the remaining probes of each probe set in each of the two or more microarray data sets;
  (4) evaluating treatment effects by performing a statistical analysis of gene expression scores between two or more groups in each of the two or more microarray data sets; and
  (5) determining concordance between the two or more microarray data sets.

16. The computer program product of claim 15, wherein each of the two or more microarray data sets is obtained from the same microarray platform.

17. The computer program product of claim 15, wherein in step (iv), the defined threshold is greater than 2, 4, 6, 8, or 10 percent outlier probes.

18. The computer program product of claim 15, wherein a critical P value squared when evaluating treatment effects for concordance is determined to yield a genome-wide, false positive rate near zero.

19. The computer program product of claim 15, wherein each of the two or more microarray data sets is obtained from substantially identical microarray platforms.

20. The computer program product of claim 15, wherein each of the two or more microarray data sets is obtained from at least two different microarray platforms.

21. The computer program product of claim 15, wherein each of the two or more microarray data sets is obtained from an DNA array, a cDNA array, a RNA array, a protein array, a tissue array, or a chemical compound array.

22. A computer implemented method comprising: analyzing quantitatively concordance between two or more microarray data sets, wherein the two or more microarray data sets comprise data from independent microarray experiments based on a plurality of replicate microarray chips, and wherein the analyzing step comprises:
  (1) evaluating outlier probe values in each of the two or more microarray data sets using a computer processor, wherein the evaluating comprises:
    (i) applying data transformation on the microarray data sets to satisfy underlying assumptions for statistical analysis, wherein the assumptions for statistical analysis are normality of error variance and homogeneity of error variance across the range of signal intensities;
    (ii) applying data normalization to correct for global differences in fluorescence levels among microarray chips,
    (iii) removing data from replicate microarray chips from the analysis that contain a percentage of outlier probe values for that microarray chip greater than a defined threshold,
    (iv) reiterating steps (i)-(iii) whenever the data from a replicate microarray chip is removed in step (iii) until there are no more chips with a percentage of outlier probe values above the defined threshold, and
    (v) masking the data on all remaining microarray chips by removing from further analysis the values of all replicates of probes that include at least one outlier;
  (2) determining a gene expression score for the remaining probes of each probe set in each of the two or more microarray data sets;
  (3) evaluating treatment effects by performing a statistical analysis of gene expression scores between two or more groups in each of the two or more microarray data sets; and
  (4) determining concordance between the two or more microarray data sets.

23. A computer program product, comprising a non-transitory computer usable medium having a computer readable program code embodied therein, said computer readable program code adapted to be executed to implement a method, said method comprising analyzing quantitatively concordance between two or more microarray data sets, wherein the two or more microarray data sets comprise data from independent microarray experiments based on a plurality of replicate microarray chips, and wherein the analyzing step comprises:

(1) evaluating outlier probe values in each of the two or more microarray data sets using a computer processor, wherein the evaluating comprises:
  (i) applying data transformation on each of the two or more microarray data sets to satisfy underlying assumptions for statistical analysis, wherein the assumptions for statistical analysis are normality of error variance and homogeneity of error variance across the range of signal intensities;
  (ii) applying data normalization to correct for global differences in fluorescence levels among microarray chips,
  (iii) removing data from replicate microarray chips from the analysis that contain a percentage of outlier probe values for that microarray chip greater than a defined threshold,
  (iv) reiterating steps (i)-(iii) whenever the data from a replicate microarray chip is removed in step (iii) until there are no more chips with a percentage of outlier probe values above the defined threshold,
  (v) masking the data on all remaining microarray chips by removing from further analysis the values of all replicates of probes that include at least one outlier;
(2) determining a gene expression score for the remaining probes of each probe set in each of the two or more microarray data sets;
(3) evaluating treatment effects by performing a statistical analysis of gene expression scores between two or more groups in each of the two or more microarray data sets and
(4) determining concordance between the two or more microarray data sets.

* * * * *